United States Patent [19]

Amlong

[11] 3,976,067
[45] Aug. 24, 1976

[54] GAS DISPENSING ASSEMBLY
[75] Inventor: William R. Amlong, Miami, Fla.
[73] Assignee: Safety Laboratories, Inc., Miami, Fla.
[22] Filed: July 2, 1974
[21] Appl. No.: 485,692

[52] U.S. Cl. ............................ 128/203; 128/142.2; 137/505
[51] Int. Cl.[2] ........................................ A61M 16/00
[58] Field of Search ... 128/203, 145.8, 146.3–146.5, 128/142, 142.3, 142.2, 202, 201, 205, 209–211; 137/505, 505.38, 505.39, 614.05, 613, 505.42; 267/123, 161; 220/3 R, 4 E

[56] References Cited
UNITED STATES PATENTS

| | | | |
|---|---|---|---|
| 1,848,232 | 3/1932 | Swope et al. | 128/145.8 |
| 2,100,778 | 11/1937 | Heidbrink | 128/203 |
| 2,117,952 | 5/1938 | Gourdou | 128/202 |
| 2,171,973 | 9/1939 | Debor | 220/3 |
| 2,421,460 | 6/1947 | Merker et al. | 220/3 |
| 2,819,728 | 1/1958 | Gage et al. | 137/505.39 |
| 3,043,302 | 7/1962 | Spears et al. | 128/203 |
| 3,114,388 | 12/1963 | Hoen | 267/161 |
| 3,186,407 | 6/1965 | Morrison | 128/203 |
| 3,386,458 | 6/1968 | Wasserman et al. | 128/145.8 |
| 3,482,591 | 12/1969 | Dufresne | 267/161 |
| 3,881,480 | 5/1975 | Lafourcade | 128/145.6 |

FOREIGN PATENTS OR APPLICATIONS

| | | | |
|---|---|---|---|
| 1,231,734 | 10/1960 | France | 128/203 |
| 349,859 | 3/1922 | Germany | 128/203 |
| 253,961 | 7/1926 | United Kingdom | 128/203 |

*Primary Examiner*—Robert W. Michell
*Assistant Examiner*—Henry J. Recla
*Attorney, Agent, or Firm*—Ladas, Parry, Von Gehr, Goldsmith & Deschamps

[57] ABSTRACT

A gas dispensing assembly suitable for dispensing oxygen from a vessel pressurized to 1800 pounds per square inch, the assembly including a manually operable eccentric member to turn supply of oxygen from said vessel on and off, a demand valve supplied with gas at the pressure inside of the vessel when the supply is turned on, a spring biased resilient diaphragm regulator operable to control the opening and closing of the demand valve to regulate the pressure in a regulator chamber to a desired pressure, an orifice through which the gas passes from the regulator chamber to an outlet valve which is opened by a demand for gas to supply the gas from the orifice to the interior of a face mask; the assembly being capable of supplying oxygen to the face mask for a period exceeding 15 minutes at a flow rate exceeding 6 liters per minute with very little variation of that flow rate with variations of pressure of the supply of oxygen.

10 Claims, 4 Drawing Figures

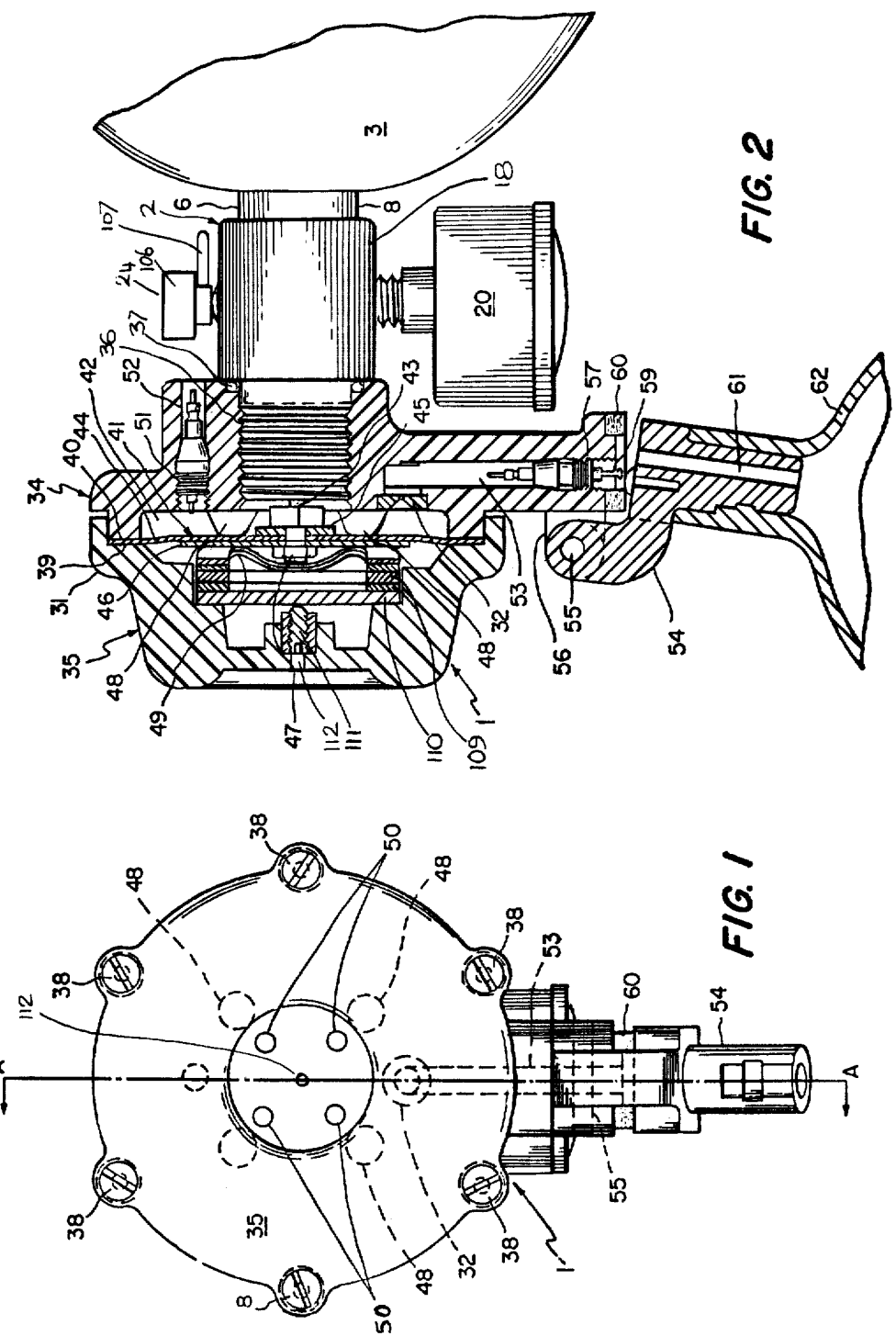

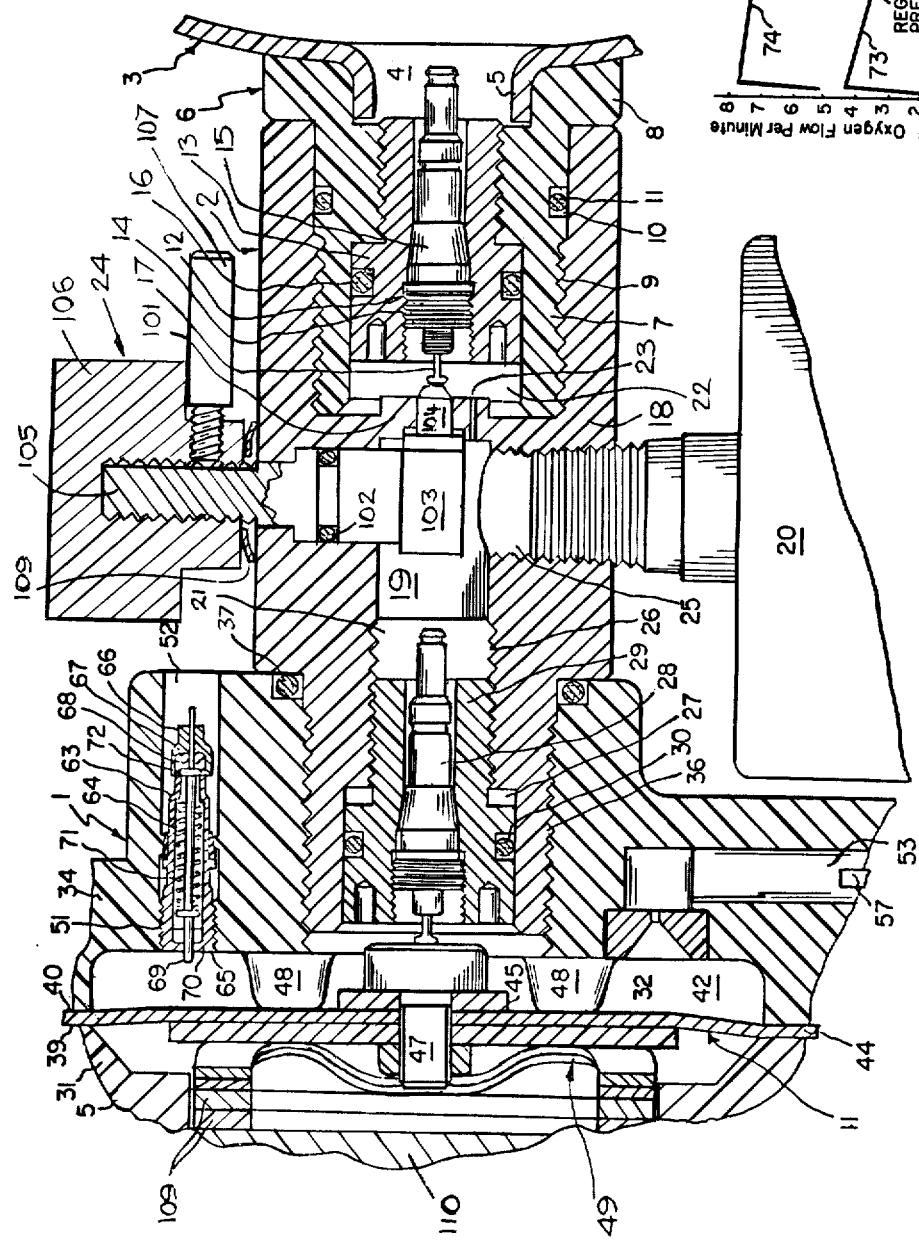

GAS DISPENSING ASSEMBLY

FIELD OF THE INVENTION

This invention relates to a gas dispensing assembly and particularly, though not exclusively, to a dispenser for dispensing oxygen on demand from a storage vessel to a face mask.

BACKGROUND

A typical example of a prior art oxygen supplying assembly is shown in U.S. Pat. No. 3,186,407 (a similar disclosure is found in Canadian Pat. No. 751,725). This prior art device meters oxygen from a vessel through an orifice and supplies this oxygen to a face mask by way of a demand valve. The rate of supply of oxygen to the face mask varies substantially with changes in the supply pressure and under many circumstances insufficient oxygen will be supplied to a user in the absence of adequate inhalation by the user. The operational characteristics of the earlier device are not satisfactory and do not meet the requirements of today for the operation of such devices.

Attention is also drawn to U.S. Pat. Nos. 3,547,143, 2,674,829, 2,906,288, 2,819,728, 3,482,591, 2,119,473, 3,538,930, 3,386,458, 3,587,642 and 2,565,560, all of which relate to various aspects of regulators.

It is an object of the present invention to provide a gas dispensing assembly capable of dispensing, on demand, at least six liters per minute of oxygen from a pressurized storage vessel of oxygen with little change in supply rate with changes in the pressure of the oxygen supply as the vessel is emptied.

It is also an object of the present invention to provide a technical and operational advance over the prior art devices such as that disclosed in U.S. Pat. No. 3,186,407 and the other U.S. Patents made of record above.

BRIEF DESCRIPTION OF INVENTION

According to one aspect of the invention a self-contained oxygen dispensing assembly comprises a housing defining an inlet passage, adapted for connection to a source of oxygen at a high pressure, and an outlet passage, a supply control means mounted in said housing to control oxygen flow from said source to said inlet passage, an inlet demand valve disposed in said inlet passage to control gas flow from said source through said inlet passage, a resiliently biased diaphragm regulator disposed in said housing and together with said housing defining a pressure regulation chamber with which, by way of said inlet demand valve, said inlet passage communicates, said regulator being arranged to control said inlet demand valve to control flow of high pressure gas from said inlet passage to regulate pressure in said chamber to a desired pressure, an orifice connecting said chamber to said outlet passage, an outlet demand valve disposed in said outlet passage to allow gas flow through the outlet passage from the chamber only when open, an outlet demand valve control member defining a supply passage and pivotally mounted to said housing for pivotal movement between an outlet demand valve opening position in which said supply passage communicates with said outlet passage and a non-operative position in which said outlet demand valve is not opened by said control member, a face mask mounted on said control member to receive oxygen from said outlet passage by way of said supply passage when said control member opens said outlet demand valve.

INTRODUCTION TO THE DRAWINGS

The invention will now be described, by way of example, with reference to the accompanying drawings, in which:

FIg. 1 is an end elevation of an oxygen dispensing assembly according to the invention;

FIG. 2 is an elevation of the assembly shown in FIG. 1 partially sectioned along section line A.A. and a fragmentary view of an oxygen storage vessel (not shown in FIG. 1);

FIG. 3 is a sectional elevation along section line A.A. of a portion of the assembly shown in FIG. 1 and a fragmentary sectional view of an oxygen storage vessel (not shown in FIG. 1); and FIG. 4 is a graphical representation of typical performance characteristics of an oxygen dispensing assembly according to the present invention.

DETAILED DESCRIPTION

Referring to FIGS. 1, 2 and 3 of the drawings, an oxygen dispensing assembly includes a regulating and outlet control arrangement 1, a connector and pressure gauge assembly 2 and a gas storage vessel 3.

In this preferred example, the oxygen storage vessel is a hollow steel sphere of a size which will contain approximately 130 liters of available oxygen when filled to 1800 pounds per square inch. The sphere is constructed from two overlapping hemispherical pressings copper brazed together, one of the pressings being formed with a central opening 4 defined by a collar 5, integrally formed with that hemisphere, to which and the surrounding portion of that hemisphere a vessel outlet valve assembly 6 is copper brazed.

The vessel outlet valve assembly 6 includes a tubular member 7 having a flange 8, to which the spherical vessel is copper brazed at one end and a threaded periphery 9 adjacent the other end. Between the threaded periphery and the flange is an external annular groove 10 which houses an O-ring seal 11. Housed within the tubular member 7 and also forming part of the vessel outlet valve assembly 6 is a demand valve 12 and a demand valve support 13. The demand valve 12 is of a type well known in the art and variously known as a "Dill" or "Schrader" valve. This demand valve 12 has a threaded portion 14 by means of which it is mounted in a cooperating screw thread of the demand valve support 13. The demand valve 12 is sealed to the demand valve support by an annular frusto-conical resilient seal 15 and is held normally closed by a spring (not shown) and gas pressure inside the vessel 3.

The demand valve support 13 is attached to the tubular member 7 by screw threads and leakage of gas between the tubular member and the demand valve support is prevented by an O-ring 16 housed in an annular external groove in the demand valve support and cooperating with both the demand valve support and the tubular member.

The demand valve 12 is opened only by an axial force applied to an operating stem 17 in a direction toward the vessel 3 sufficient to overcome the valve closing force resulting from the combined action of the spring mentioned above and the gas pressure in the vessel.

The connector and pressure gauge assembly 2 is attached by screw threads to threads 9 of the vessel 3 and is sealed thereto by O-ring 11 comprises an elongate substantially cylindrical member 18 having a passage 19 extending longitudinally therethrough and a pressure gauge 20 connected to the elongate cylindrical member 18 by screw threads and communicating with the passage 19 to provide an indication of gas pressure in the passage 19. The passage 19 provides communication from the vessel 3 by way of demand valve 12 to the regulating and outlet control arrangement 1. The passage 19 comprises two axial portions 21 and 22 separated by a web 101 and an offset portion 23 extending through the web to provide communication between the two axial portions. A manually operable demand valve operating member 24 extends through the wall of member 18 into the passage 19. Gas leakage past the member 24 is prevented by an O-ring 102 housed in an annular groove in the member 24 between the member 24 and the member 18. The member 24 is of a generally cylindrical form and is arranged for rotation about its longitudinal axis within the member 18. The portion of member 24 within the passage 19 includes an eccentric 103 arranged on rotation of member 24 to depress a stud 104 which extends centrally through web 101 to depress the stem 17 of demand valve 12 to open said valve upon further rotation or reversal of rotation of member 24 to allow valve 12 to close under the influence of the gas pressure in vessel 3 and the spring of valve 12. The member 24 includes a threaded stem 105 extending outwardly from member 18 to which is screwed a knob 106. The knob is locked to the stem by a locking screw 107 the outer end of which operates as an indicator of the rotational position of eccentric 103. The offset portion 23 of the passage 19 provides communication between the two axial portions 21 and 22 past the centrally located and axially extending stud 104. The knob 106 is spaced from member 18 by a disked spring washer 108.

A radial passage 25 extending from the passage 19 and having screw threads therein provides for the mounting of the pressure gauge 20 and the communication of that pressure gauge with the passage 19.

The axial portion 21 of the passage 19 is the portion of the passage remote from the vessel 3 when the connector and pressure gauge assembly 2 is connected to the pressure vessel. The portion 21 of the passage 19 is provided with internal screw threads 26 and a counterbore 27, the threads and counterbore being adapted to receive a demand valve 28 and a demand valve support 29 which in construction, operation and methods of sealing are substantially identical to the demand valve 12 and demand valve support 13.

The demand valve 28 and demand valve support 29 form a part of the regulating and outlet control arrangement 1 and when mounted in the elongate cylindrical member 18 are sealed to that member by an O-ring 30 housed in an external annular groove in the demand valve support 29 and cooperating with this groove and the internal cylindrical surface of the counterbore 27.

The regulator and outlet control arrangement 1 includes a spring biased diaphragm regulator 31, an orifice 32 and an outlet valve arrangement 33.

The regulator includes two housing members 34 and 35, the member 34 of which includes a threaded bore 36 mounted on a threaded exterior portion of the end of the elongate cylindrical member 18 having the screw threads 26 and counterbore 27. Leakage of oxygen between the housing member 34 and the elongate cylindrical member is prevented by an O-ring seal 37 housed in a counterbore in the housing member 34 and cooperating with an annular shoulder formed on the elongate cylindrical member.

Housing member 35 is a spring housing cap connected to housing member 34 by six screws and nuts 38 (shown only in FIG. 1). Clamped by the screws 38 between cooperating annular surfaces 39 and 40 of the two housing members 34 and 35 is a circular diaphragm 41. The diaphragm together with the housing member 34 dfines a regulator chamber 42 with which, by way of demand valve 28, passage 19 and demand valve 12, the interior of vessel 3 communicates. The stem 43 of demand valve 28 extends along the longitudinal axis of the connector and pressure gauge assembly 2 to the chamber 42 and toward the center of the diaphragm 41, the plane of the diaphragm when undistorted being normal to said longitudinal axis and the diaphragm being coaxially mounted with said longitudinal axis.

The diaphragm comprises a circular oxygen impervious resilient member 44, of canvas, coated and impregnated on both sides with an elastomer such as "Buna(n)", sandwiched between two substantially rigid steel discs 45 and 46, the discs and the resilient member being coaxially mounted and held together at said longitudinal axis by a nut and bolt 47. The head of the bolt of the nut and bolt 47 is a plain cylindrical disc arranged when the diaphragm is in the position shown in the drawing to engage the stem 43 of demand valve 28 thereby to open the demand valve 28. Integrally formed with the housing member 34 and extending into the chamber 42 symmetrically about and parallel to the longitudinal axis are four stops 48 arranged to limit the maximum deflection of the diaphragm along the longitudinal axis toward the vessel 3.

The disc 45 adjacent the bolt head of the nut and bolt 47 is small enough in diameter to pass inside the symmetrically arranged stops 48.

On the side of the diaphragm 41 remote from the chamber 42 and housed in the housing member 35 is a coal spring 49 comprised of two superimposed wave spring washers. The longitudinal axis of spring 49 is coincident with the longitudinal axis of the connector and pressure gauge assembly and the line of action is along that axis. The spring 49 is backed by spacer washers 109 which engage a disc 110. The spring, washers and disc are radially located by housing member 35 and spring tension is controlled by an adjusting screw 111 mounted in said housing member 35 and extending along the longitudinal axis of the connector and pressure gauge assembly into engagement with the center of disc 110. Access to said screw 111 for adjustment of spring tension is by way of an opening 112 in said housing member 35. The housing member 35 has four vent holes 50 of sufficient size to substantially eliminate any differences in pressure between the interior and the exterior of the housing member 35.

The spring pressure, dimensions and resilience of the diaphragm and position and operating characteristics of the valve 28 are coordinated so that the regulator will provide a regulated pressure in the chamber 42 within the range from 12 to 16 pounds per square inch above ambient pressure with a pressure in the passage 19 in the range of from 20 to 1800 pounds per square inch above ambient pressure.

A relief valve 51 is mounted in a passage 52 extending from the chamber 42 to the exterior of the housing member 34. The relief valve 51 is of substantially the same construction as demand valves 12 and 28 and is arranged to open in response to a pressure differential exceeding 25 pounds per square inch. The relief valve is provided in order to relieve pressure in chamber 42 in the event that a valve failure elsewhere in the gas dispensing assembly results in the pressure in the chamber 42 exceeding ambient pressure by 25 pounds per square inch.

In an alternative embodiment the relief valve 51 is replaced by a rupture disc arranged to rupture at a desired pressure. The rupture disc may be mounted in, molded in or integrally formed as part of the housing member 34.

An outlet passage 53 extends from the chamber 42 to the outlet valve arrangement 33 by way of the orifice 32 which is 0.025 inches in diameter. The orifice 32 is in a member mounted in the housing member 34.

The orifice is such that flow of oxygen therethrough will always be turbulent when the pressure in the chamber 42 exceeds ambient pressure by at least 12 pounds per square inch, the size of the orifice being sufficient to provide an oxygen flow rate through the orifice in the range from 6 to 8 liters per minute with a pressure in the chamber 42 in the range from 12 to 16 pounds per square inch above ambient pressure.

As the flow through the orifice is always turbulent in the operating range of the assembly and the flow rate through the orifice is primarily dependent only on the magnitude of the pressure in the chamber 42 above ambient pressure, the oxygen dispensing assembly here described will provide a flow of oxygen at a rate which is substantially independent of ambient pressure.

The outlet passage 53 extends from the orifice 32 in a direction normal to the longitudinal axis of the connector and pressure gauge assembly 2 through an extension of the housing member 34. A mask mounting member 54 is pivotally mounted by a pin 55 and mounting lug 56 adjacent the end of said extension. The lug 56 is integrally formed with the extension.

Inside the outlet passage 53 is an outlet valve 57 of a type well known to those skilled in the art and similar in construction to the demand valves 12 and 28 and the relief valve 51. A valve operating stud 58 is embedded in the mask mounting member and projects from the mask mounting member toward the extension of the housing member 34 to cooperate with the valve operating stem 59 of the outlet valve 57 when the mask mounting member is pivoted toward the extension in a direction anti-clockwise about pin 55 as seen in FIGS. 2 and 3. To the end of the extension surrounding the end of the outlet passage 53 is attached an annular resilient seal constructed of a closed cell foamed "Neoprene" arranged to cooperate with the extension and the mask mounting member when the outlet valve is opened by the stud to prevent any substantial leakage of oxygen between these members, thereby ensuring that oxygen flowing from the linear orifice 32 through the outlet passage 53 past the open valve 57 flows through a passage 61 extending through the mask mounting member 54 to the interior of a breathing mask 62 which is mounted on the mask mounting member 54.

The mask 62 (a portion of which is shown only in FIG. 2) is adapted to cover the nose and mouth of a user for the purpose of supplying oxygen thereto.

Valves 12, 28, 51 and 57 are all of a type well known to those skilled in the art and have the following features in common (described here specifically with reference to valve 51, the only valve shown in section in the drawings). The valve has a valve body 63 of generally cylindrical form longitudinally through which extends a passage 64 for the flow of fluid. At one end 65 of the valve is an external screw thread for mounting the valve in a housing and at the other end 66 of the valve is an annular valve seat against which when the valve is closed rests a closure member 67 having a resilient seal 68 of annular form to cooperate with the valve seat to prevent passage of fluid between the seat and the closure member 67 when the valve is closed. Connected to the closure member 67 and extending throughout the length of the valve to project from the end 65 is a valve stem 69. The valve stem is slideably supported in the end 65 of the valve, which end is shaped to form a bridge portion 70 to permit passage of fluid from the end of the valve while supporting the stem on the longitudinal axis of the valve. A flange on the stem in the passage 64 abuts one end of a coil spring 71 housed in the passage and acting between the said flange and the body 63 of the valve to bias the valve to an operating condition in which the closure member 67 is sealed against the valve seat. The resilient seal 68 is housed in a cup shaped recess of the closure member 67 about the stem 69 which extends completely through the closure member to which it is rigidly attached and is maintained in position by a flange 72 on the valve stem adjacent the valve seat.

A valve of this type is held in a normally closed position by the coil spring and is opened either by mechanical movement of the stem (to the right as seen in FIG. 2) or by a pressure differential across the closure member 67 sufficient to overcome the bias of the coil spring 71. In the case of valves 12, 28 and 57, it is mechanical movement of the stem which opens the valve, any pressure across the valve acting in a direction such that the pressure differential tends to keep the valve closed. As opposed to the operation of those three valves, the relief valve 51 is opened by a pressure differential across the closure member, acting in a direction which opposes the spring bias, when that pressure differential is sufficient to overcome the spring bias.

Demand valves 12 and 28 operate at the high pressure present in the vessel 3 and the resilient seal of these valves is of a material suitable for use with oxygen at high pressure. An example of this material is an elastomer compound sold under the trade name "Viton". The resilient seals of the relief valve 51 and outlet valve 57 are required to operate at relatively low pressures in relation to the demand valves 12 and 28 and the material requirements for their resilient seals are less stringent and may be met by a number of resilient sealing materials well known to those skilled in the art (e.g., an elastomer such as "Buna(n)").

On the exterior of the body 63 is a resilient annular frusto-conical seal which seals the valve body to a housing for that body by compression of the seal, against an annular abutment in the body, when the valve is screwed into valve accommodating screw threads in the body.

The two housing members 34 and 35 and the mask mounting member 54 are moldings of a plastics material known as ABS and are chromium plated, the mask is a molding of linear polyethylene, and the elongate cylindrical member is chromium plated steel.

In operation, when the oxygen dispensing assembly is screwed onto the vessel 3 and member 24 is turned to an on position the eccentric 103 depresses stud 104 and the stud 104 spans demand valve 12 thereby allowing oxygen from the vessel 3 into the passage 19. The oxygen in the passage 19 has substantially the same pressure as the oxygen in the vessel 3 and this pressure is indicated by the pressure gauge 20. The pressure differential across demand valve 28 together with the spring pressure applied by the biasing spring of demand valve 28 and the force generated on the diaphragm by the pressure in the regulator chamber 42 above ambient pressure oppose the spring force applied by spring 49 to the diaphragm. The arrangement is such that when the pressure in passage 19 is in the range from 20 to 1800 pounds per square inch above ambient pressure the diaphragm will control opening of the demand valve 28 to maintain a pressure in the chamber 42 in the range from 12 to 16 pounds per square inch above ambient pressure.

When the face mask and mask mounting member are pivoted against the light resistance of the resilient seal 60 to open the outlet valve 57, oxygen will flow from the chamber 42 through the orifice 32 past the valve 57 and through the passage 61 to the face mask. This flow will continue until the vessel is empty or the outlet valve is allowed to close and any excess oxygen not required by the user of the mask will escape through vent holes (not shown) provided in the mask.

FIG. 4 is a graphical representation of the operational characteristics of a typical valve as hereinbefore described by way of example. The base of the graph indicates the pressure of oxygen in the vessel 3, the left hand margin indicates rate of oxygen flow into the mask in liters per minute and the right hand margin indicates oxygen pressure in the regulator chamber 42. Line 73 indicates the relationship between the oxygen supply pressure and the pressure in the regulator chamber 42. The variation of this pressure with supply pressure results from the change in differential pressure across demand valve 28 as the oxygen supply in the vessel 3 diminishes and its pressure consequently drops. The rapid dip to zero at the low pressure end of the oxygen supply of curve 73 represents the regulated pressure when the oxygen supply pressure has dropped below a supply pressure of approximately 20 pounds per square inch above ambient pressure.

Line 74 indicates the relationship between rate of oxygen flow with the outlet valve 57 open in relation to oxygen supply pressure in the vessel 3. The low slope of this curve over a very wide range of supply pressure represents one of the primary advantages of the combination of features of the present invention and provides a substantial advance in the art whereby over a supply pressure range of 20 to 1800 pounds per square inch above ambient pressure an output flow rate varying only from about 6 liters per minute to about 8 liters per minute can be achieved (in the example given in FIG. 4 a range of only from 6.2 liters per minute to 7.5 liters per minute was achieved). As with line 73, the rapid drop of line 74 with low oxygen supply pressures results from the vessel pressure dropping to 20 pounds per square inch and thus becoming, in substance, empty.

As can be seen from FIG. 4, the output flow rate in liters per minute is substantially proportional to the oxygen supply pressure and to the regulated pressure in the regulator chamber 42.

I claim:

1. A self-contained oxygen dispensing assembly comprising a housing defining an inlet passage having first and second ends, and an outlet passage, an interchangeable high pressure oxygen supply vessel removably connected to said first end of said inlet passage to supply oxygen thereto said vessel having an outlet demand valve, a supply control means mounted in said inlet passage and operable to open said vessel demand valve to control oxygen flow from said source to said inlet passage, an inlet demand valve disposed in said inlet passage adjacent said second end to control gas flow from said source through said inlet passage, a resiliently biased diaphragm regulator disposed in said housing at the second end of said inlet passage and including a pressure regulation chamber said second end of said inlet passage terminating in said pressure regulation chamber, said regulator including means providing operable cooperation between said inlet demand valve and said diaphragm for controlling said inlet demand valve to control flow of high pressure gas from said inlet passage whereby the pressure in said chamber is regulated to a desired pressure, an orifice connecting said chamber to said outlet passage, an outlet demand valve disposed in said outlet passage to allow gas flow through the outlet passage from the chamber only when open, an outlet demand valve control member defining a supply passage said supply passage being in alignment with said outlet passage; said control member being pivotally mounted to said housing for pivotal movement between an outlet demand valve opening position in which said supply passage communicates with said outlet passage and a nonoperative position in which said outlet demand valve is not opened by said control member, a face mask mounted on said control member to receive oxygen from said outlet passage by way of said supply passage when said control member opens said outlet demand valve.

2. An assembly according to claim 1, wherein said regulator comprises a circular resilient diaphragm the periphery of which is attached and sealed to said housing, a wave spring washer means housed in said housing on the side of said diaphragm remote from said chamber and acting between said housing and said diaphragm to oppose force applied to said diaphragm by pressure of gas in said chamber and to bias said diaphragm in a direction which will open said inlet demand valve when the gas pressure in said chamber is below said desired pressure.

3. An assembly according to claim 2, wherein a plurality of diaphragm stops project from said housing into said chamber to limit deformation of said diaphragm toward said inlet control valve and a relief means is located in said housing, said relief means being adapted to respond to a pressure differential across said relief valve in excess of a desired magnitude to relieve an excessive pressure condition in said chamber.

4. An assembly according to claim 1, wherein said orifice has a diameter of 0.025 inches thereby to provide a gas flow within the orifice, when the outlet demand valve is open, which is always turbulent while the gas pressure in said chamber is within its normal range of variation.

5. An assembly according to claim 1, wherein said supply control means comprises a member rotatably mounted in a sealed manner through said housing, an operating knob attached to said member exteriorly of said housing to facilitate rotation of said member and a stud slideably mounted in said housing and extending between said member and the vessel demand valve, said member having an eccentric portion positioned in contact with said stud to slide said stud upon rotation of said member by said knob to open said vessel demand valve and upon further rotation to allow said stud to return to a position in which said vessel demand valve is closed.

6. An oxygen dispensing assembly according to claim 1, wherein said vessel is a spherical tank having an outlet assembly adapted for connection to said housing to provide communication from said vessel to said inlet passage, said outlet assembly including said demand valve and an annular O-ring seal to seal said housing to said outlet assembly.

7. An oxygen dispensing assembly according to claim 1, further comprising an annular resilient closed pocket foam seal attached to said housing and adapted to seal said housing to said control member when said outlet demand valve is open to ensure that substantially all oxygen from the outlet passage passes into said supply passage.

8. An oxygen dispensing arrangement according to claim 1, wherein said vessel is a spherical tank, which when full is pressurized to 1800 pounds per square inch, having an oxygen capacity of 130 liters at 1800 pounds per square inch, said gas dispensing assembly is adapted to dispense said oxygen on demand at at least about 6 liters per minute for a total dispensing time exceeding 15 minutes.

9. An oxygen dispensing arrangement according to claim 8, wherein said regulator is adapted to maintain a pressure of oxygen in said chamber in a range from about 12 pounds per square inch above ambient pressure to about 16 pounds per square inch above ambient pressure with a variation of pressure in said inlet passage in a range from about 20 pounds per square inch above ambient pressure to about 1800 pounds per square inch above ambient pressure and said orifice is dimensioned and constructed to pass oxygen, when said outlet demand valve is open, at a rate in a range from about 6 liters per minute to about 8 liters per minute with said range of pressure in said chamber.

10. An assembly according to claim 1, wherein said housing comprises a steel connector member defining said inlet passage, adapted for connection to a source of high pressure gas and housing said inlet demand valve and first and second housing members constructed of chromium plated plastics moldings, said first of said housing members being attached to said connector portion, defining, with the diaphragm of said regulator, said chamber, housing said linear orifice, having an integral extension defining said outlet passage and housing said outlet demand valve, and being attached to said second of said housing members to clamp and seal the edge of said diaphragm therebetween.

* * * * *